United States Patent [19]

Goel et al.

[11] Patent Number: 4,507,243

[45] Date of Patent: Mar. 26, 1985

[54] MANUFACTURE OF ARYL ESTERS

[75] Inventors: Anil B. Goel, Worthington; Peter E. Throckmorton, Plain City, both of Ohio

[73] Assignee: Ashland Oil, Inc., Ashland, Ky.

[21] Appl. No.: 468,311

[22] Filed: Feb. 22, 1983

[51] Int. Cl.³ ............................ C09F 5/08; C07C 67/00
[52] U.S. Cl. .................................. 260/410.5; 560/131
[58] Field of Search ................ 568/802, 470; 560/131; 260/410.5; 203/50, 53

[56] References Cited

U.S. PATENT DOCUMENTS 3,646,111  2/1972  Hornig et al. .................... 568/802

Primary Examiner—Anton H. Sutto
Attorney, Agent, or Firm—John F. Jones

[57] ABSTRACT

The oxidation process for the manufacture of aryl esters comprising contacting the reaction mixture of an aromatic hydrocarbon, a carboxylic acid and molecular oxygen in the liquid phase at an elevated temperature with a catalyst composed of palladium or a compound of palladium, a chromium compound and a compound of at least one member selected from the group consisting of zinc, manganese, tin, cobalt and nickel is described.

12 Claims, No Drawings

MANUFACTURE OF ARYL ESTERS

BACKGROUND OF THE INVENTION

1. Field of the Invention

The present invention provides an improved process for making aryl esters from aromatic hydrocarbons such as benzene, naphthalene, anthracene, biphenyl, phenanthrene, fluorene, terphenyls, and the like, which comprises the reaction of a mixture of an aromatic hydrocarbon, molecular oxygen, a carboxylic acid, and optionally a hydrocarbon solvent, in the liquid phase in the presence of a catalyst which is composed of palladium or a compound of palladium, a compound of chromium and a compound of at least one metal selected from the group consisting of Zn, Mn, Sn, Co, and Ni.

2. Description of the Prior Art

The manufacture of phenol by the direct oxidation of benzene with oxygen is known. There are, for instance, thermal processes which are performed at very high temperatures in which the phenol formed is susceptible to further oxidation so that considerable loss of yield occurs as is disclosed in U.S. Pat. No. 2,223,383. In the presence of catalysts, the oxidation can be carried out at somewhat lower temperatures as in U.S. Pat. No. 3,133,122 but the reactions have been plagued by low conversions and excessive production of unwanted by-products as is disclosed in U.S. Pat. No. 2,392,875.

It has been proposed to make phenyl acetate and biphenyl from benzene and acetic acid in the liquid phase in the presence of palladium acetate and without added molecular oxygen by a stoichiometric reaction in *Chem. and Ind.*, Mar. 12, 1966, page 457.

U.S. Pat. No. 3,542,852 discloses the preparation of hydroxy aromatic compounds by reaction of an aromatic compound and oxygen in the presence of a catalyst composed of iron, a noble metal or a compound of either in the presence of a nitrate ion and a carboxylic acid. More recently the preparation of phenyl esters and phenols by the reaction of benzene, molecular oxygen and a lower aliphatic carboxylic acid in the presence of a catalyst composed of a Group VIII metal (U.S. Pat. No. 3,642,873) or a compound of such metal (U.S. Pat. No. 3,651,127) have been disclosed. Similarly variations in this type of reaction have been disclosed in U.S. Pat. Nos. 3,646,111; 3,651,101; 3,772,383; 3,959,352 and 3,959,354. U.S. Pat. No. 3,959,354 concludes that liquid phase reactions of this type, because of problems of catalyst elution, etc., are disadvantageous for an industrial process. U.S. Pat. No. 3,772,383 describes a liquid phase reaction using a very complex catalyst system which includes the use of nitric acid and a lower aliphatic carboxylic acid such as acetic, propionic, butyric, etc. U.S. Pat. No. 3,644,486 describes the catalytic manufacture of oxacylation products and optionally hydroxylation products of condensed aromatic compounds, saturated aliphatic or cycloaliphatic carboxylic acids and molecular oxygen in the presence of a noble metal of Sub-Group VIII of the Mendeleef Periodic Table or compounds thereof. This Patent also discloses that transition metals can be used with the Group VIII metals and that carbonates or acylates of alkali or alkaline earth metals may also be used as activators in the catalyst system. Although extremely low yields of hydroxylation product are shown.

Generally speaking, these prior art processes deal for the most part with vapor phase oxidation reactions, or liquid phase reactions in which all of the reactants (except oxygen in some instances) are initially included in the reaction mixture and they use lower alkyl carboxylic acids such as acetic acid and propionic acid. Moreover, in general the prior art catalytic processes have produced low conversions, usually less than 10%, with poor selectivity to the desired aryl ester, and the hydroxy aromatic compound, such as phenol or naphthol, is often a primary product. The use of the lower saturated carboxylic acids, primarily acetic acid, in the catalytic oxidation process produces a highly corrosive system which can cause reaction equipment corrosion problems and excessive recyle costs as well as the extremely poor conversions and selectivities mentioned above. None of the prior art methods disclose the continuous addition of the aromatic hydrocarbon, the continuous removal of water from the reaction mixture as it forms, nor do they disclose or suggest the use of a solvent or the applicants' catalyst for the higher aromatic compounds in Applicants' process.

SUMMARY OF THE INVENTION

We have discovered an improved oxidation process for the transformation of aromatic hydrocarbons such as benzene, naphthalene, anthracene, biphenyl, phenanthrene, terphenyls, fluorene, and the like, molecular oxygen and a higher carboxylic acid to the corresponding aromatic carboxylate in good conversions and selectivities to the desired product by including using a catalyst system composed of a compound of palladium, a compound of chromium and a compound of at least one metal selected from the group consisting of Zn, Mn, Sn, Co, and Ni. Our process also may use a solvent for the aromatic hydrocarbon, particularly when the aromatic hydrocarbon is one containing 10 or more carbon atoms and two or more aromatic rings per molecule such as naphthalene, anthracene, biphenyl, phenanthrene, terphenyls, fluorene, and the like. It is in our preferred process that a mono or polycarboxylic acid having 5 or more carbon atoms be used.

Our liquid phase reaction produces good yields of aryl esters, particularly when the water that is formed as the aromatic hydrocarbon is converted to ester is continuously removed in the process. If water, which is a by-product of the oxidation reaction, is allowed to remain in the reaction mixture, it can cause hydrolysis of the aryl ester to produce aromatic hydroxy compounds which in turn can cause fouling and inactivation of the catalyst.

The catalysts useful in our process are preferably composed of palladium metal or compounds of palladium and usually a palladium carboxylate for convenience in conjunction with a chromium compound usually a chromuim carboxylate and a compound usually a carboxylate of at least one metal selected from the group consisting of zinc, manganese, tin, cobalt and nickel. The catalysts of this invention may be used alone or may be supported on a carrier or support material. Suitable carriers include silica, alumina, carbon, quartz, pumice, diatomaceous earth, and the like and others which are known in the art.

The carboxylic acids useful in our invention include mono and poly-carboxylic acids having from 5 to 30 carbon atoms which correspond to the formula $R(COOH)_n$ wherein n is an integer of 1 to 5 and R is a hydrocarbon group having at least 5-n carbon atoms. Most preferred are monocarboxylic acids in which n is 1 and R is an aliphatic hydrocarbon group having from 7 to 19 carbon atoms. Some carboxylic acid anhydride can be included with the carboxylic acid in the reaction if desired.

For the higher aromatic hydrocarbons organic solvents which may be useful for the entrainment and removal of water from the reaction mixture include linear hydrocarbons having the formula $C_nH_{2n+2}$ wherein n is from 4 to 14 such as heptane, pentane, octanes, and the like, cyclic hydrocarbons having the formula $C_nH_{2n}$ wherein n is from 4 to 14, and linear and cyclic aliphatic ethers.

The process of this invention produces in the case of benzene reactant conversions of the carboxylic acid to ester in the order of about 10% with selectivities to the phenyl ester on the order of 95%. The phenyl esters which are produced by our process can be readily converted to the corresponding phenol and the corresponding carboxylic acid by known methods for hydrolysis. Phenol is easily recovered by known means and the corresponding carboxylic acid is readily recycled for further use in the oxidation reaction of this invention.

DESCRIPTION OF THE PREFERRED EMBODIMENT

In a typical reaction in accordance with this invention benzene and the carboxylic acid are contacted with the catalyst in an oxygen containing atmosphere at a reaction temperature in the range of from about 100° to 300° C. and preferably from about 140° to 200° C. and at from about 1 to 100, preferably 1 to 10 atmospheres and most preferably at or near atmospheric pressure. The molecular oxygen can be oxygen, per se, or any gaseous mixture containing molecular oxygen. For instance, molecular oxygen can be in the form of air for convenience. The catalyst can be in the form of a mixture of palladium acetate, chromium acetate and at least one of zinc acetate, manganese acetate, tin acetate, cobalt acetate and nickel acetate. The molar ratio of Pd:Cr:M wherein M is a member selected from the group consisting of zinc, manganese, tin, cobalt, and nickel should be in the range of from 1.0:0.1:0.1 to 1:20:20 and preferably in the range of from 1:0.2:0.2 to 1:10:10. During the reaction the water formed as a by-product is continuously removed conveniently by entrainment with excess benzene or with the organic solvent when it is used. The benzene or organic solvent is continuously distilled from the reaction mixture as the reaction proceeds. The major product, phenyl carboxylate, can be hydrolyzed to produce phenol and the carboxylic acid and catalyst can be recycled back for reuse in the oxidation reaction.

Because essentially no phenol is produced directly in the oxidation reaction of this invention, it is believed that catalyst activity is maintained for long periods of time under continuous use. The rapid removal of water from the reaction mixture is probably at least partly responsible for the absence of phenol in the oxidation reaction product. The presence of phenol in the oxidation reaction mixture is believed to be detrimental in causing catalyst fouling and catalyst inactivation which result in very short catalyst life. The process of this invention is further illustrated in the following examples.

EXAMPLE 1

To a 250 ml 3-neck flask equipped with a mechanical stirrer, reflux condenser and Dean-Stark tube were charged 0.67 g. (0.003 mol) of palladium (II) acetate, 0.66 g. (0.003 mol) of zinc acetate, 0.74 g. (0.003 mol) of chromium (III) acetate monohydrate, 39.81 g. (0.276 mol) of octanoic acid and 4.09 g. (0.051 mol) of benzene. The resulting mixture was stirred and heated to 170° C. and oxygen was bubbled through the reaction mixture at a flow rate of about 50 cc/minute. Water formed during the reaction and was removed continuosly as it formed by azeotropic distillation with the excess benzene. The reaction temperature was maintained at 170° C.±2° C. during the course of the reaction and additional benzene was fed to the reactor by pump at a slow rate. The reaction was carried out for 5 hours and the total benzene was 17.5 g. (0.225 mol). GLC analysis of the reaction mixture after 5 hours reaction time showed the formation of phenyl octanoate (19 millimols) and of some phenylene bisoctanoyloxy esters o,m,p, combined) (3.9 millimols total) for a total of 26.8 m mol of phenyl ester (about 10% conversion of the octanoic acid).

EXAMPLE 2

This example demonstrates that a catalyst composed only of palladium and chromium compounds is inferior to the catalysts composed of compounds of palladium, chromium and a compound of a member from the group consisting of zinc, manganese, tin, cobalt and nickel. The procedure given in Example 1 was followed except that the catalyst was composed of 0.67 g. of palladium (II) acetate (0.003 mol), and 0.74 g. of chromium (III) acetate. GLC analysis of the reaction mixture after 5 hours reaction time showed that only 5 millimols of the phenyl ester of octanoic acid (2% conversion) had taken place

EXAMPLES 3-6

The procedure of Example 1 was followed except that instead of 0.003 mol of zinc (II) acetate the same amount (0.003 mol) of the acetates listed in the following table were used as part of the catalyst system. The amount of phenyl ester and the mols of phenyl ester per mol of palladium (in 5 hours reaction time) for each example are also given in the following table:

TABLE

| Example | Metal Acetate in Catalyst | Phenyl Ester M Mols | Mols of Ester Per Mol of Palladium |
|---|---|---|---|
| 3 | $Sn^{II}$ | 22 | 7.3 |
| 4 | $Mn^{II}$ | 19 | 6.2 |
| 5 | $Co^{II}$ | 20 | 6.6 |
| 6 | $Ni^{II}$ | 17.5 | 5.8 |

We claim:

1. An oxidation process for the manufacture of aryl esters comprising contacting the reaction mixture of an aromatic hydrocarbon, a carboxylic acid and molecular oxygen in the liquid phase at a temperature in the range of from 100° to 300° C. with a catalyst composed of A palladium carboxylate, a chromium carboxylate and a carboxylate of at least one member selected from the group consisting of zinc, manganese, tin, cobalt and nickel wherein the molar ratio of Pd:Cr:Zn, Mn, Sn, Co or Ni is in the range of from 1.0:0.1:0.1 to 1:20:20.

2. The process of claim 1 wherein the aromatic compound is selected from the group consisting of benzene, naphthalene, anthracene, biphenyl, phenanthrene, fluorene, and terphenyls.

3. The process of claim 2 wherein the carboxylic acid is one which corresponds to the formula $R(COOH)_n$ wherein n is an integer of from 1 to 5 and R is a hydrocarbon group having at least 5-n carbon atoms.

4. The process of claim 3 wherein n is 1 and R is an aliphatic hydrocarbon group having from 7 to 11 carbon atoms.

5. The process of claim 4 wherein the water formed in the oxidation reaction is continuously removed from the reaction mixture.

6. The process of claim 5 wherein the aromatic hydrocarbon is benzene.

7. The process of claim 6 wherein the carboxylic acid is octanoic acid.

8. The process of claim 7 wherein the catalyst is composed of palladium acetate, chromium acetate and zinc acetate.

9. The process of claim 7 wherein the catalyst is composed of palladium acetate, chromium acetate and tin acetate.

10. The process of claim 7 wherein the catalyst is composed of palladium acetate, chromium acetate and manganese acetate.

11. The process of claim 7 wherein the catalyst is composed of palladium acetate, chromium acetate and cobalt acetate.

12. The process of claim 7 wherein the catalyst is composed of palladium acetate, chromium acetate and nickel acetate.

* * * * *